United States Patent [19]

Tencza et al.

[11] Patent Number: 4,851,230
[45] Date of Patent: Jul. 25, 1989

[54] CAPSULE SHAPED TABLETS

[75] Inventors: Thomas M. Tencza, Wallington; Mahesh Patell, Edison; F. Henry Merkle, Scotch Plains, all of N.J.

[73] Assignee: Bristol-Myers Company, New York, N.Y.

[21] Appl. No.: 8,807

[22] Filed: Jan. 30, 1987

Related U.S. Application Data

[63] Continuation of Ser. No. 483,051, Apr. 7, 1983.

[51] Int. Cl.[4] .............................................. A61K 9/44
[52] U.S. Cl. ................................................... 424/467
[58] Field of Search ........................................ 424/467

[56] References Cited

U.S. PATENT DOCUMENTS 4,591,500  5/1986  Scapinelli ........................... 424/467

OTHER PUBLICATIONS

Ansel, "Introduction to Pharmaceutical Dosage Forms", Lea & Febiger, Phila, Pa. (1969, pp. 274–309, Capsules Tablets, Pills and Miscellaneous Solid Dosage Forms.

Primary Examiner—Shep K. Rose
Attorney, Agent, or Firm—Gene Warzecha

[57] ABSTRACT

A capsule shaped tablet containing a pharmaceutically active ingredient in which the tablet has a cap portion and a body portion physically bound to each other; the cap portion having a larger outside diameter than the body; the tablet may be provided with a coating of a film forming polymer to simulate a hard gelatin capsule dosage form.

3 Claims, 1 Drawing Sheet

CAPSULE SHAPED TABLETS

This is a continuing application of application Ser. No. 483,051, filed on Apr. 7, 1983.

This invention relates to tablets and particularly to film coated capsule shaped tablets.

Dispensing pharmaceutical products as powders and/or granules contained in gelatin capsules has gained wide acceptance in the pharmaceutical industry. More recently, consumers of over-the-counter (OTC) drugs have also demonstrated a preference for taking these OTC drugs as powders or granules in a gelatin capsule. However, the recent rash of cases of tampering with OTC drugs in gelatin capsules has presented the pharmaceutical industry with a serious problem. On the one hand, these powdered drugs in a gelatin capsule are a highly acceptable dosage form and yet there are distinct dangers inherent in this kind of a dosage form, particularly for pharmaceutical products sold OTC.

It has now been found that this dilemma can be alleviated by forming a powdered and/or granular mix containing one or more pharmaceutical agents into a tablet having a true capsule shape (i.e. having body and cap portions in which the outside diameter of the cap portion is greater than the outside diameter of the body) and then preferably applying a film coating to the capsule shaped tablet which simulates both the appearance and function of the gelatin capsule.

It is accordingly an object of the present invention to provide a tamper proof pharmaceutical dosage form having the simulated form and function of a capsule.

It is also an object of the present invention to provide a tamper proof dosage form in which a mix of materials containing one or more pharmaceutically active ingredients is formed into a capsule shaped tablet having a true capsule shape and preferably then coating the capsule shaped tablet with a film forming agent to simulate the appearance and function of a gelatin capsule.

Other and more detailed objects of this invention will be apparent from the following description, drawings and claims.

In the attached drawings, in which the same numerals designate the same structure in the various views.

Figure 1:
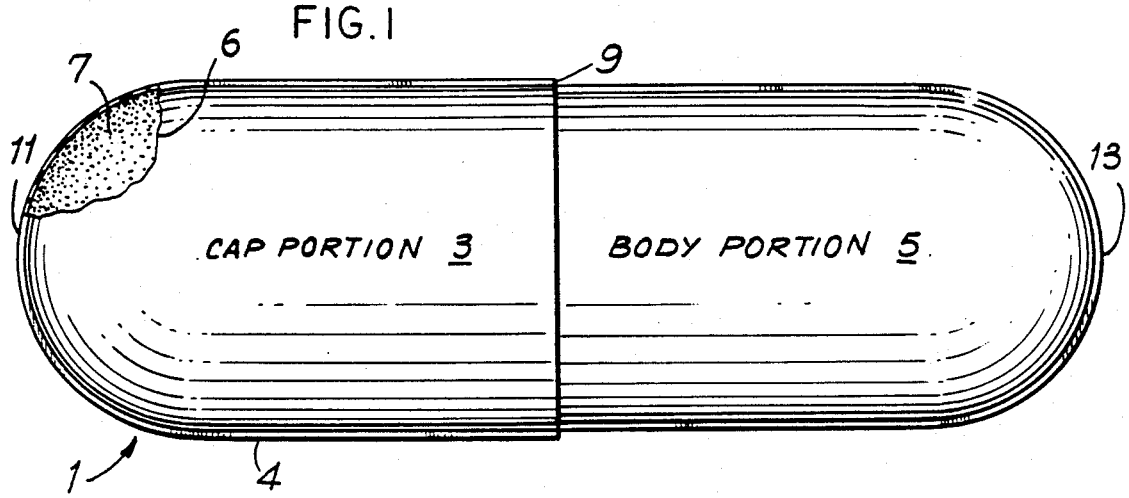
FIG. 1 is a top plan view of a film coated capsule shaped tablet embodied in the present invention, part of the coating being shown as removed to expose the underlying tablet.

Forming a tablet into a cylindrical dosage form and providing this with a coating is known in the prior art. Typical examples of tablets of this character are shown in the Physicians Desk Reference, 34th Edition, 1980, pg. 434 (See THERAGRAN tablets). These, however, do not have the appearance of a true capsule having a cap and body portion nor do they simulate the function of a gelatin capsule.

Referring to the drawings in which the same parts in the various views have the same designation, the film coated capsule shaped tablet is shown generally at 1. This comprises a cap portion 3 and a body portion 5. Film coated tablet 1 is formed by compressing a powdered or granular mixture containing pharmaceutical ingredients into a capsule shaped tablet 7 shown in cross section in FIG. 4.

The profile of tablet 7 (albeit film coated) is seen in FIG. 1 and comprises cap portion 3 which is physically bound to a body portion 5 to form a unitary tablet. The outer diameter of cap portion 3 is greater than the outer diameter of body portion 5 along a major portion of their respective long axes. Because of these dimensions, a lip 9 is formed at the juncture of cap portion 3 and body portion 5. This gives the tablet the appearance of a true capsule.

The dimensions of tablet 7 may vary somewhat. In general, however, the overall length will be in the range of from about 11 mm. to about 22 mm. with the preferred length being from about 16 mm. to about 19 mm.

The outer end 11 of cap portion 3 and the outer end 13 of body portion 5 will have curved profiles so as to simulate a capsule. The radius of curvature of these end portions may vary somewhat. Usually, however, the radius of curvature of end 11 will be from about 2.8 mm to about 3.20 mm.; the radius of curvature for end 13 will also be from about 2.8 to about 3.2 mm.

As indicated above, the outside diameter of cap portion 3 will always be a little greater than the outer diameter of body portion 5. Generally, the cap portion 3 will have a diameter of from about 5.3 mm to about 8.5 mm and preferably from about 6.9 mm to about 7.6 mm; whereas, the body portion 3 will have an outside diameter from about 5.1 mm to about 8.2 mm, the preferred diameter being from about 6.6 mm to about 7.3 mm. For the most part, the outside diameter of cap portion 3 will be from about 0.05 mm to about 0.30 mm greater than the outside diameter of body portion 5. This preferred difference is from about 0.125 mm to about 0.210 mm.

In preparing the capsule shaped tablets in accordance with the present invention, a granulation or other compressible powdered material is compressed in an appropriately shaped die between appropriately shaped upper and lower die punches. These punches and dies are designed to form a tablet having the configuration shown in FIGS. 1 through 3. It is advisable during this compression process to stop the die punch margins or edges of the upper and lower tablet punches from coming in contact with each other since this would tend to destroy the punches. The consequences of this procedure i.e. halting the compression before the die punch margins meet is to form a slightly elevated band 4 around the longitudinal equator of tablet 1.

The pharmaceutically active ingredients that may be contained in the tablets of the present invention can be any of a large variety of materials. The only limitation on this material is that it is able to be incorporated into a mixture that is capable of being tabletted. By way of example of active pharmaceutical ingredients that may be incorporated in the present tablets, there may be mentioned: analgesics, decongestants, antihistamines, antitussives, antacids, gastric protectants, appetite suppressants, bronchodilators, hematinics, sleep aids, sleep suppressors, vitamins, laxatives, antibiotics, antispasmodics, etc. and mixtures thereof. It is particularly useful in conjunction with such therapeutically active materials as aspirin, acetaminophen; combinations of aspirin and acetaminophen; combinations of aspirin with buffers, combinations of acetaminophen, phenylpropanolamine HCl, chlorpheniramine maleate, dextromethorphan HBr; combinations of aspirin and phenylephrine HCl; combinations of aspirin, acetaminophen, salicylamide and caffeine; the combination of acetaminophen and pyrilamine maleate; the combination of aspirin, phenylpropanolamine and chlorpheniramine maleate; caffeine; vitamin combinations, etc.

In addition to the pharmaceutically active ingredients described above, the tablets of the present invention may also contain other conventional tablet additives and aids. These include such ingredients as granulating agents, fillers, lubricating agents, disintegrants, surface active agents, coloring agents, flavoring agents, glidents, etc.

The capsule shaped tablets of the present invention may be prepared in a variety of ways. The procedure may follow one or a combination of several well established methodologies such as:

(a) direct compression from primary powder mixtures or from granules which are also prepared by dry compaction; or (b) wet granulation utilizing a solution of a powder binder which is mixed with the drug ingredient plus excipients to produce agglomerates or granules. The granules are subsequently dried and sized into a blend suitable for compression.

Figure 2:
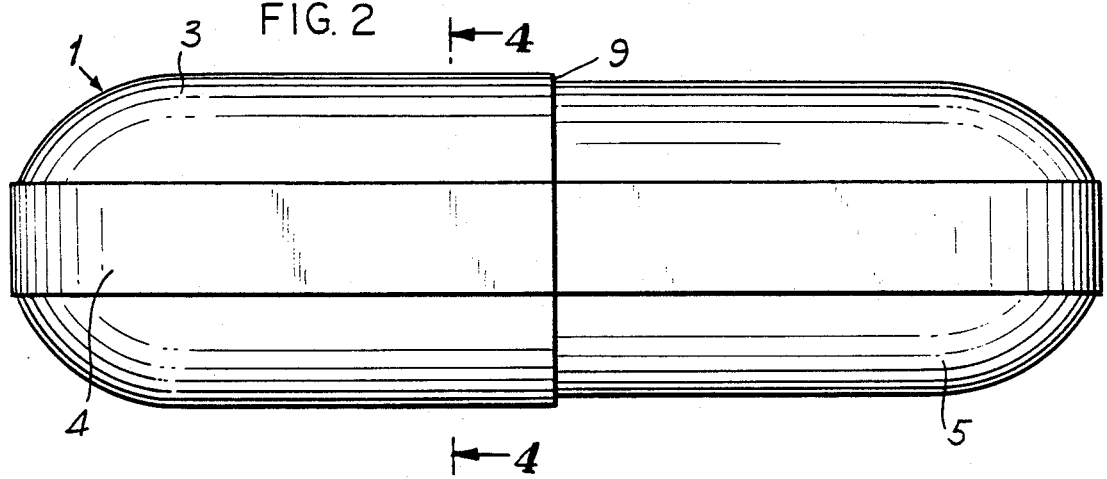
FIG. 2 is a side elevation of the film coated capsule shaped tablet shown in FIG. 1.
Figure 3:
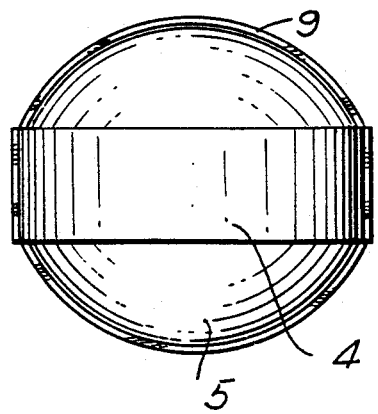
FIG. 3 is an end view of the film coated capsule shaped tablet shown in FIG. 2 as viewed from the right side of FIG. 2.

In any event, the final formation of the compressed tablet entails the use of well known tablet compressing machines which, by utilizing steel punches and dies and the application of high pressures, compress the powder mixture and/or granulation into a tablet of a specific shape or design as, for example, shown in FIGS. 1 through 3.

As indicated above, a feature of the present invention is to coat the capsule shaped tablet with a film forming polymeric substance which will simulate the appearance and function of a gelatin capsule. A number of film forming materials are known in this art which will serve this purpose. By way of example, the following may be mentioned: methylcellulose, hydroxypropyl methylcellulose, PVP (Povidone), ethylcellulose (Ethocel 10 CPS), EUDRAGIT E 30D, EUDRAGIT L 30D, *PHARMACOAT 606 6CPS, OPADRY, COTERIC, cellulose acetate phthlate. However, the film forming polymers of choice are hydroxypropyl methycellulose 5-15 cps, PHARMACOAT 6 CPS (Shin-Estu Co.) alone or in combination with ethylcellulose 10 CPS and PVP.

The thickness of the coating of film forming polymer that is applied to the capsule shaped tablet of this invention may vary. The only essential limit is that it be able to simulate the appearance and function of a gelatin capsule. In the case where quick absorption of the active pharmaceutical agents contained in the tablet is desired, this will be taken into account in determining the thickness of the film coating. Usually, the thickness of the polymer coating on the capsule shaped tablet will be within the range of from about 0.0127 mm to about 0.127 mm with the preferred range being from about 0.025 mm to about 0.075 mm.

The coating of film forming polymer may be applied to the capsule shaped tablets according to the present invention in a number of ways. Usually, it will be applied using a solution or suspension of the film forming polymer in a solvent. Generally, the film forming polymer will be present in said solvent or suspending medium in the range of from about 4% to about 15% by weight based on the total weight of the coating solution or composition. This may vary with the nature of the solvent system employed. In non-aqueous systems, the film forming polymer may be present at a level in the range of from about 4% to about 6% on the same weight basis with the preferred level being from about 4.5% to about 5%. In the case of aqueous solvent systems, the polymer will usually constitute between about 8% to about 15% by weight based on the total weight of the coating solution or composition.

*Hydroxypropyl methylcellulose viscosity 6 CPS

A variety of solvents or solvent systems may be employed as the carrier for the film forming polymer during the coating operation. These may be aqueous or organic solvent systems. By way of example, the following may be mentioned: water; isopropyl alcohol plus methylene chloride; methanol plus methylene chloride, etc.

In applying the film forming polymer coating to the capsule shaped tablets in accordance with this invention, any of the known techniques may be employed. The film coating may be performed using any one of several types of equipment such as conventional coating pan, Accela-Cota, Hi-Cota or Wurster air suspension column. All these equipment should have an exhaust system to remove dust and solvent or water vapors to facilitate quick drying.

Spray guns or other suitable atomizing equipment may be introduced into the coating pans and rigidly fixed in a desired position to provide spray patterns conductive to rapid and uniform coverage of the tablet bed. Normally, heated or cold drying air is introduced over the tablet bed in a continuous or alternate fashion with a spray cycle to expedite drying of the solution.

The coating solution may be sprayed by using pneumatic or hydraulic spray pump system in a continuously or intermittent spray-dry cycle which is controlled by the use of timers, punch tapes or solenoid valves. The type of spray application usually depends on the drying efficiency of the coating pan.

In most cases, the coating material is sprayed until the tablets are uniformly coated and the desired increase in weight is achieved to impart the required coating properties and appearance to the tablet core. Many different types of coatings may be applied such as enteric; slow release or rapidly dissolving type for fast acting tablets.

Figure 4:
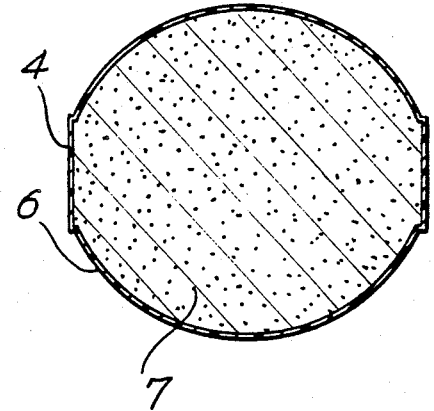
FIG. 4 is a cross-sectional view of the coated tablet shown in FIG. 2 taken along line 4—4.

The polymeric film coating applied to the capsule shaped tablets according to the present invention is designated as 6 in the drawings and is best seen in FIGS. 1 and 4. In FIG. 1, the edge of the film coating 6 is seen; a portion of this coating having been broken away to expose the underlying tablet 7. In FIG. 4 film coating 6 is shown in cross section. The relative thickness of coating 6 is somewhat exaggerated so that it can be seen in the drawing.

The following Examples are given to further illustrate the present invention. It is to be understood, however, that this invention is not limited thereto.

EXAMPLE 1

Uncoated Capsule Shaped Buffered Aspirin Tablets
(Tablet Cores PP 873C-01-74

A batch (46,285) two-layer buffered aspirin tablets is prepared as follows:

| Dosage Unit Amt. mg/tab | Item No. | Ingredients | % Layer | % Total Tab |
|---|---|---|---|---|
| | | Layer I (aspirin granulation) | | |
| 324.000 | 1. | Aspirin 80 mesh | 84.749 | 35.982 |

| Dosage Unit Amt. mg/tab | Item No. | Ingredients | % Layer | % Total Tab |
|---|---|---|---|---|
| 57.348 | 2. | Starch, corn | 15.001 | 6.369 |
| 0.956 | 3. | Sodium lauryl sulfate, phos. buffered | 0.250 | 0.106 |
| 382.304 | | | 100.000 | (42.457) |
| | | Layer II (buffer granulation | | |
| 225.000 | 4. | Magnesium carbonate | 44.955 | 24.987 |
| 200.000 | 5. | Calcium carbonate | 39.960 | 22.211 |
| 25.000 | 6. | Starch, corn (as 10% starch paste | 4.995 | 2.776 |
| 48.000 | 7. | Starch, corn | 9.590 | 5.331 |
| 2.500 | 8. | Castor oil, hydrogenated powder | 0.500 | 0.278 |
| | 9. | Water, deionized | | |
| 500.000 | | | 100.000 | (55.583) |
| 882.804 | | | | 98.040 |

Procedure:

Layer I (Granulation)

Granulated without further modification.

Layer II (Granulation)

1. Blend 4 & 5 and granulate with 6, adding additional water as required.
2. Pass wet mass through Tornado Mill (5/16" screen) dry in fluid bed dryer.
3. Pass dry granulation through Oscillator (10 mesh screen, 0.059" opening).
4. Add 7 & 8, blend well.

Granulations for Layers I and II are fed sequentially into a tablet die provided with a lower tablet punch. The granulations are then compressed by an upper tablet punch to form a two-layer tablet. The tablet die and tablet punches are tooled to form a capsule shaped tablet shown in FIGS. 1 to 3 of the drawings. The specifications for this tablet are as follows:

Punch: Cap. 281" × 0.750" × 0.060"
Weight: 882.804 mg. CORES
Thickness: 0.255" + 0.005"
Hardness: 14–16 SCU (Heberlein)
Disintegration: USP Basket App., Water 37° C.—35–45 sec.

EXAMPLE 2

Film Coated Capsule Shaped Buffered Aspirin Tablets

A batch of tablets (11,330) prepared according to Example 1 above were film coated using the composition and process described below.

| Dosage Unit Amt. mg/tab | Item No. | Ingredients | % of Film Coating | % Total Tab |
|---|---|---|---|---|
| 882.804 | | Part I Tablets from Example 1 | | (98.0357) |
| | | Part II Film Coating | | |
| (216.623)* | 10. | Methylene chloride | | * |
| 11.931 | 11. | Hydroxypropyl methylcellulose E-15 Premium** | 67.452 | 1.3249 |
| (111.714)* | 12. | Methanol | | * |
| 1.326 | 13. | "Plasticizer Blend"*** | 7.497 | 0.1473 |
| 4.381 | 14. | Opaspray - Yellow K-1-2184 (containing 36.72% solids in #3A alcohol*) | 24.768 | 0.4865 |
| 0.050 | 15. | "Polishing Wax" | 0.283 | 0.0056 |
| 17.688 | | (Carnauba Wax powder) | 100.000 | 1.9643 |
| 900.492 | | | | 100.0000 |
| | | ***"Plasticizer Blend" Composition | | |
| 0.707 | | Propylene glycol | 3.9971 | 0.0785 |
| 0.266 | | Mineral oil, 55–65 SUS | 1.5038 | 0.0296 |
| 0.353 | | Tween 80 | 1.9957 | 0.0392 |
| 1.326 | | | 7.4966 | 0.1473 |

*does not add to tablet weight

Preparation

1. Blend propylene glycol with Tween 80 in a stainless steel container using lightening mixer.
2. Add mineral oil 55–65 SUS to the above blend and mix well.

Part II-Film Coating

Preparation

1. Disperse item 11 in item 10 (2.454 kilos) using lightening mixer, then add item 12 (1.266 Gms) to make clear solution.
2. Add items 13 and 14 (135.2 Gm), mix well to make homogenous color suspension.

Application

1. Place tablets in coating pan with baffles and exhaust. Heat to 42°–45° C.
2. Film coating solution is sprayed through a spray gun while drying until all of the solution is sprayed.
3. Tablets are cooled to room temperature in the coating pan with exhaust.

Polishing

Polish tablets by sprinkling item 15 in pan, mix 5 minutes.

Specifications for the coated tablets prepared in accordance with this Example are as follows:
Weight: 900.492 mg.
Thickness: 0.262" ± 0.005"
Disintegration: USP Basket App., Water 37° C. ≈ 1 min.

EXAMPLE 3

Film Coating Capsule Shaped Tablets Using Aqueous Film Coating

Capsule shaped tablets prepared in accordance with Example 1 are film coated with the coating composition described below. The coating procedure is essentially the procedure given in Example 2.

Aqueous Film Coating-12.5% Solids: CE 3096-18

| Ingredients | Gms/6000 gms | % w/w |
|---|---|---|
| 1. Water DI | 3200 | 53.334 |
| 2. Methocel E-5 premium* | 480 | 8.000 |
| 3. PVP | 93 | 1.550 |
| 4. Sodium lauryl sulfate | 20 | 0.333 |
| 5. Water DI | 2050 | 34.167 |
| 6. Propylene glycol | 80 | 1.333 |
| 7. Mineral oil - light | 2 | 0.033 |

| Ingredients | Gms/6000 gms | % w/w |
| --- | --- | --- |
| 8. Tween 80 | 5 | 0.083 |
| 9. Color conc. C&W blue | 70 | 1.167 |
| | 6000 | 100.000 |

Add 1 gm Antifoam AF emulsion if required to prevent foaming

Process for preparing Aqueous Film Coating CE 3096-18

Dissolve 3 & 4 in hot water—item 1
Add 2 while water is hot—hydrate completely
Add item 5—cool to room temperature
Mix 7, 8 and 9 together—mix well
Add to coating solution
Mix well—slowly to avoid foam

EXAMPLE 4

Film Coating Capsule Shaped Buffered Aspirin Tablet with Three Way Polymer Rapid Release Film Coating System Capsule shaped tablets prepared in accordance with Example 1 are film coated with the composition described below. The coating procedure is essentially the procedure given in Example 2.
*Methylcellulose Formula CE 1822-36

| Ingredients | % w/w |
| --- | --- |
| Methylene chloride | 60.00 |
| Methocel 15 cps* | 1.50 |
| Ethocel 10 cps | 1.50 |
| PVP | 1.50 |
| Methanol | 30.00 |
| Sodium lauryl sulfate | 0.50 |
| Magnesium carbonate | 1.00 |
| Propylene glycol | 0.75 |
| Mineral oil, light | 0.25 |
| Tween 80 | 0.25 |
| Opaspray Yellow K-1-2184 | 2.75 |
| | 100.00 |

EXAMPLE 5

Uncoated Capsule Shaped Acetaminophen Tablets (Formula CE 3096-36)

An acetaminophen mixture was prepared having the following formula:

| Ingredients | mg/tablet |
| --- | --- |
| Acetaminophen powder | 500.00 |
| PVP | 5.00 |
| Corn starch | 50.55 |
| Stearic acid | 2.00 |

| Ingredients | mg/tablet |
| --- | --- |
| Total tablet wt. | 557.55 |

This mixture was used to prepare uncoated capsule shaped acetaminophen tablets using essentially the same tabletting procedure described in Example 1. The specifications for these tablets are as follows:
Thickness: cap portion ~0.253"; body portion ~0.231"
Hardness: ~18 to 22 SCU
Disintegration: less than 10 minutes
Friability: ~0.22%

EXAMPLE 6

Aqueous Film Coated Capsule Shaped Acetaminophen Tablets (Formula CE 3096-41)

The uncoated tablets prepared in accordance with Example 5 are film coated using the following coating composition:

| Ingredients | mg/tablet |
| --- | --- |
| Uncoated core tablet above (CE 3096-36) | 557.550 |
| PVP | 2.041 |
| Hydroxylpropylmethyl-cellulose, 5 cps | 10.883 |
| Propylene glycol | 1.496 |
| Arlacel - 20 | 0.812 |
| Tween - 20 | 0.612 |
| Mineral oil, light | 0.816 |
| Color, soluble dye | 0.068 |
| Total tablet wt. | 574.278 |

The coating procedure is essentially that described in Example 2. These tablets have the following specifications:
Thickness: cap portion ~0.255"; body portion ~0.233
Disintegration: less than 12 minutes Although the invention has been described with reference to specific forms thereof, it will be understood that many changes and modifications may be made without departing from the spirit of this invention.

What is claimed is:

1. Pharmaceutical tablet, consisting essentially of a blend of one or more excipients and one or more active substances in the form of granules, compressed into the shape of a capsule comprising two semicapsules, each provided with a head or ogive, and having a step at the juncture between the two semicapsules which together form the tablet.

2. Tablet according to claim 1, wherein the tablet may be divided into portions determined by the step which is present at the connecting point or juncture between the two semicapsules which together form the tablet.

3. Tablet according to claim 2, wherein the tablet may be divided into two halves which may be severed along the said step.

* * * * *